United States Patent [19]

Ayers et al.

[11] 4,096,136

[45] Jun. 20, 1978

[54] METHOD OF SELECTIVELY REMOVING LIPOPROTEIN FROM BLOOD PLASMA OR SERUM USING SULFATED CARBOHYDRATE ION-EXCHANGERS

[76] Inventors: John Stephen Ayers, 45 Pahiatua St.; David Roderick Husbands, 73 Church St., both of Palmerston North, New Zealand

[21] Appl. No.: 773,270

[22] Filed: Mar. 1, 1977

[30] Foreign Application Priority Data

Mar. 4, 1976 New Zealand ........................ 180199

[51] Int. Cl.² ............................................... C07G 7/00
[52] U.S. Cl. ................................. 260/112 B; 424/101; 424/177; 23/230 B
[58] Field of Search ................... 260/112 B; 424/101, 424/177

[56] References Cited

U.S. PATENT DOCUMENTS

| | | | |
|---|---|---|---|
| 3,562,289 | 2/1971 | Battista et al. | 260/112 R |
| 3,573,277 | 3/1971 | Grant | 260/112 R X |
| 3,838,143 | 9/1974 | Grant | 260/112 R |
| 3,842,061 | 10/1974 | Andersson et al. | 260/112 B |
| 3,920,625 | 11/1975 | Andersson et al. | 260/112 B |

OTHER PUBLICATIONS

Methods in Enzymology, vol. XXII, Jakoby, 1971, pp. 273–285.
Introduction to Modern Biochemistry, 3rd Edition, Karlson, 1968, pp. 395–396.
Chem. Abstracts, vol. 71, 1969, 114440q, Sjovall et al.

*Primary Examiner*—Howard E. Schain
*Attorney, Agent, or Firm*—Holman & Stern

[57] ABSTRACT

The invention relates to the use of a sulphated ion exchanger to selectively remove lipoproteins from blood plasma or serum. Although the attraction between sulphate groups and proteins has long been recognized it has now unexpectedly been found that cationic ion exchangers whose ion exchange capacity is provided by sulphate groups bind lipoproteins selectively in presence of other plasma or serum proteins and ions when they are equilibrated with solutions containing divalent cations and the same cation is added to the plasma or serum. Types of ion exchanger matrices and applications of the utility are discussed.

17 Claims, 6 Drawing Figures

METHOD OF SELECTIVELY REMOVING LIPOPROTEIN FROM BLOOD PLASMA OR SERUM USING SULFATED CARBOHYDRATE ION-EXCHANGERS

BACKGROUND OF THE INVENTION

1. Field of Invention

This invention relates to a method of selectively removing lipoproteins from blood plasma or serum.

2. Description of the Prior Art

The fractional separation of the numerous species of proteins occurring in plasma or serum has been of considerable interest to investigators for nearly a century. Advances have been made with the result that some of the protein species are now harvested industrially with a high degree of purity e.g. fibrinogen, γ-globulins and albumin. However any attempt at the isolation of one of the plasma or serum proteins is hindered by a variety of technical problems, a common one being the presence of sizeable amounts of lipoproteins. These are not easily removed selectively, least of all on a large scale.

Ion exchangers work on charge-charge interaction between the exchanger and the substance sought to be bound to the exchanger and thus isolated from the fluid. It is to be expected that where there is a plurality of species of similar charge a particular species would not be selectively removed by an ion exchanger. We have now quite unexpectedly found that cationic ion exchangers whose ion exchange capacity is provided by sulphate groups bind lipoproteins selectively in the presence of all other serum proteins and ions when they are equilibriated with solutions containing divalent cations, such as magnesium, calcium and manganese and the same divalent cation is added to the serum. The concentration of the cation required in the serum depends on the character of the matrix sulphated, the extent of the sulphation, the cation and the pH of the serum. Preferably the concentration is in the range 0.05 to 1.0 M and a pH between 6 and 8. Suitable parameters are more particularly set out in the following examples.

It has been observed that elevated plasma lipoprotein concentration is frequently a secondary phenomenon associated with primary diseases such as diabetes mellitus, hypothyroidism, heavy proteinuria and obstructive jaundice. In addition, over the past quarter century data have been gathered which tend to suggest a direct correlation between plasma lipoprotein concentration and the incidence of clinical coronary artery disease.

Lipoproteins in blood plasma comprise three primary fractions, the very low density (VLDL) fraction, the low density (LDL) fraction and the high density (HDL) fraction. A high concentration of the second of these has been observed in patients who have suffered coronary artery disease. A fuller review of this background to the invention may be found in "Blood Lipids and Lipoproteins Quantitation, Composition and Metabolism." Edited, Gary J. Nelson, John Wiley & Son Inc. U.S.A., 1972. It will be appreciated that a simple method of testing for such an abnormality as a matter of routine in an annual medical examination is highly desirable. A patient thus warned could take corrective steps such as changes in diet or commence taking medication to reduce the unwanted concentration to lessen the possibility that he might be subject to coronary disease. Methods which have been used up to now to determine the relative concentration of the fractions of the lipoproteins in blood have involved tedious precipitation and centrifugings and the quantitative resolution has been something less than satisfactory (Cf. Journal of Lipid Research, Vol 11, 1970 pp 583 to 595.

It is an object of this invention to go some way towards alleviating these disadvantages or at least to provide the public with a useful choice.

SUMMARY OF THE INVENTION

Accordingly, the invention may be said broadly to consist in a method of selectively removing lipoproteins from blood plasma or serum which comprises the following steps: associating blood plasma or serum containing divalent cations with a cationic ion exchanger, comprising a water insoluble, hydrophilic, water swellable matrix; a plurality of sulphate groups chemically bonded to said matrix, the ion exchange capacity of said exchanger being provided by said sulphate groups; said matrix comprising, either:

a cross-linked carbohydrate; a cross-linked polysaccharide or hydroxyl containing derivative thereof, or a cross-linked cellulose in any one of its native fibrous, microgranular, microcrystalline or regenerated forms or, a cross-linked carbohydrate, a cross-linked polysaccharide or hydroxyl containing derivative thereof, or a cross-linked cellulose in any one of its native fibrous, microgranular, micro-crystalline or regenerated forms, a plurality of hydroxy lower alkyl groups being chemically bonded to said carbohydrate, polysaccharide, polysaccharide derivative or cellulose, recovering lipoproteins bound to said exchanger or recovering the blood serum or plasma residue from which lipoproteins have been extracted or recovering both said extracted lipoproteins and said serum or plasma residue.

The ion exchanger and methods for its preparation are more particularly described and claimed in our United States Application No. 773,269 entitled "Sulphated Ion Exchanger and Method For Preparation thereof" filed on even date herewith. The specification and claims of our copending application No. 773,269 are hereby incorporated herein by reference.

DESCRIPTION OF THE PREFERRED EMBODIMENTS

The invention may be more fully understood by having reference to the following detailed description of the preferred embodiments thereof.

EXAMPLE 1 — MANUFACTURE OF ION EXCHANGER

A. Preparation of Hydroxypropyl Cellulose

Granular regenerated cellulose (20 g) was mixed with cold 30% (W/V) aqueous sodium hydroxide (30 ml), 2 ml epichlorohydrin (10% V/W based on cellulose) and 10 ml propylene oxide (50% V/W based on cellulose). The mixture was stirred thoroughly until the cellulose had finished swelling and all the liquid had been absorbed. The damp powdery cellulose was then placed in a container and sealed before heating it at 60° C without further mixing. After 2 hours the reaction vessel was cooled to room temperature, opened and the contents were transferred into a large volume of water (500 ml). The particles of hydroxypropyl cellulose were collected on a Buchner funnel, washed well with water and finally dried by solvent exchange into methanol and then by heating at 60° C under reduced pressure. The product (20 g) was stored in a desiccator until required for sulphation. It had a swollen bed volume of 9.5 ml/g in distilled water.

B. Preparation of Hydroxypropyl Cellulose Sulphate (Na$^+$ form)

Dry hydroxypropyl cellulose (1g), pyridine-sulphur trioxide (1g) and dry pyridine (10 ml) were placed in an Erlenmeyer flask, protected with a drying tube and heated on an oil bath at 80° C for 1.5 hours. The flask was shaken periodically by hand during the course of the reaction and then cooled before transferring the reaction mixture into 200 ml of deionized water. The sulphated product was collected on a sintered glass funnel and washed thoroughly with more deionized water. To convert it from the pyridinium to the sodium ion form it was titrated in 1 M sodium chloride with 0.1 M sodium hydroxide to a phenolphthalein end point and then recollected and washed on the filter again before storing wet at 4° C.

EXAMPLE 2 — DETERMINATION OF THE DEGREE OF SUBSTITUTION

The extent of sulphation (2.37 meq/g) was determined from the volume (31.2 ml) of 0.1 M sodium hydroxide used to neutralize the pyridinium ion displaced from the sulphated cellulose and by assuming a 100% yield of cellulose from the reaction. The validity of this was shown by carrying out a duplicate preparation and determining the dry weight of product at the end. The ion exchange capacity could be varied from 0 to 4.0 meq/g by changing the amount of pyridinesulphur trioxide complex used in the reaction.

EXAMPLE 3 — USE OF SULPHATED ION EXCHANGERS TO SELECTIVELY REMOVE LIPOPROTEINS

A column was packed with the ion exchanger, hydroxylpropyl regenerated cellulose-8-50 sulphate (1 meq/g) prepared as herein described in Example 1B. It was equilibrated with one column volume of 0.5 M magnesium chloride containing 0.01 M sodium bicarbonate and adjusted to pH 7.4. When serum diluted 1:1 with 1 M magnesium chloride and adjusted to pH 7.4 with 0.1 M sodium hydroxide, was passed through the column, two of the lipoprotein fractions, the very low density lipoproteins (VLDL) and the low density lipoproteins (LDL) were selectively and quantitatively removed. Other proteins including the third lipoprotein fraction, the high density lipoproteins (HDL), passed straight through the column and were washed out with a further column volume of the 0.5 M magnesium chloride (pH 7.4) solution as used initially to equilibrate the column. The lipoproteins (VLDL and LDL) bound to the column were eluted with a solution 0.25 M in sodium chloride and 0.25 M in trisodium citrate which had been adjusted to pH 7.4 with 1 M hydrochloric acid. (Alternatively these lipoproteins can be eluted rapidly with 1 M sodium chloride). The eluted lipoproteins were shown to be uncontaminated with other serum proteins by immunoelectrophoresis and agarose electrophoresis. Similarly the serum proteins which passed straight through the column were shown to be devoid of VLDL and LDL by immunoelectrophoresis and agarose electrophoresis.

The HDL fraction may also be retained on the column if a more highly substituted ion exchanger is used, e.g. 3-5 meq/g but this is not always necessary as it is usually the LDL and VLDL which cause the trouble in serum protein fractionations. The flow rate of serum through the ion exchange column was such that the lipoproteins can be removed from 5 ml of serum inside a 15 minute period and also larger columns can be used still with good flow characteristics. Thus quite unexpectedly from previous methods of selectively removing the lipoprotein components from serum, the use of this ion exchanger achieved it quantitatively and with speed.

Consequently if such a procedure is used first, it can facilitate the isolation of other serum proteins. For example in the preparation of IgG from serum, all other proteins are adsorbed onto a column of QAE-Sephadex leaving IgG to pass straight through the column (Protides of the biological fluids; proceedings of the 18th Colloquim, 1969, p. 511 - 515). However the volume of diluted serum loaded onto the column cannot exceed 75% of the volume of the column or LDL's and VLDL's also break through the column and contaminate the IgG. By removing the LDL's and VLDL's first on a column of sulphated ion exchanger and then carrying out the preparation of IgG as outlined in the references above, up to three times as much serum may be loaded onto the QAE-Sephadex column without contamination of the IgG being isolated.

EXAMPLE 4 — TESTING FOR ELEVATED LIPOPROTEIN CONTENT

Blood samples were obtained from normal subjects after overnight fasting. The serum was used within three or four days.

Cholesterol measurements were performed using 500 $\mu$l aliquots of column effluents reacted with 3 ml of ethanolic/KOH (88 ml of ethanol plus 12 ml of 50% KOH) at 50° C for 30 minutes. After reaction 1.5 ml of hexane and 0.5 ml of water was added and a 1,000 $\mu$l sample of organic layer was removed and evaporated to dryness. The extracted cholesterol sample was then reacted with 1 ml of Lieberman Burchard reagent (20 ml acetic anhydride: 1 ml sulphuric acid: 10 ml acetic acid) and after thirty minutes the optical density was determined at 620 nm in a 1 ml cuvette. A standard curve was constructed under similar conditions. When this method was used for serum cholesterol determination a 50 $\mu$l serum sample was sufficient.

GEL ELECTROPHORESIS — Polyacrylamide disc gel electrophoresis was conducted as follows.

The separating gel contained 3.75% acrylamide (pH 8.9) while the upper gel contained 2.5% acrylamide (pH 6.7). The sample gel was not used, samples prestained with Sudan black B were applied directly to the concentrating gel in 30% sucrose. After electrophoresis gels were overstained with 1% amido black in 7% acetic acid.

BRIEF DESCRIPTION OF THE DRAWINGS

The results of this method of testing may be more fully understood by having reference to the drawings wherein.

EXAMPLE 5

Figure 1:
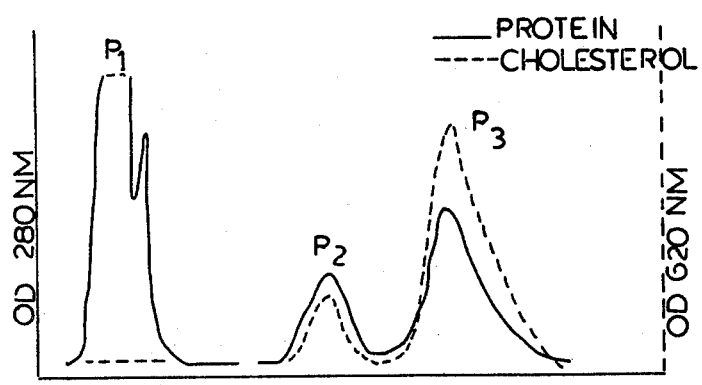
FIG. 1 is a plot of the cholesterol content of the protein fractions eluted from the sulphated ion exchanger of Example 5, below.

A sulphated ion exchanger with a sulphate content of 3.7 meq/g, prepared from hydroxypropyl cellulose was packed in a column (8 × 1 cm) and equilibrated with 25 ml of 0.5 M $MgCl_2$. 2 ml of human serum was brought to 0.5M in $MgCl_2$ and applied to the column, which was then washed with 25 ml of 0.5M $MgCl_2$ followed by 10 ml of 0.05M $MgCl_2$. As the sample was applied to the column the semitranslucent resin became opaque. This was later found to be due to VLDL and LDL binding. The bound protein was eluted with a linear gradient consisting of 60 ml 0.1M NaCl and 60 ml 1M NaCl. Five ml fractions were collected. A 500 μl sample was taken from each tube and its cholesterol content was determined as a means of assaying for lipoproteins (FIG. 1).

Figure 2:
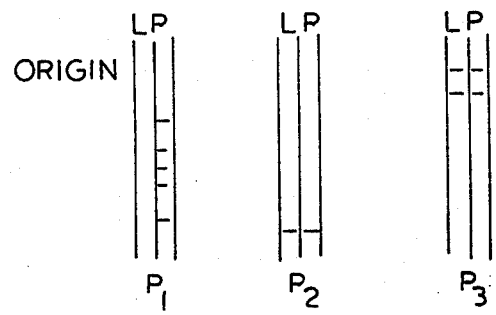
FIG. 2 is the electrophoresis pattern of the three protein peaks eluted from the sulphated ion exchanger of Example 5, below. The right hand gel, P, of each pair was stained for protein, the left hand gel, L, was stained for lipid.

The non-bound protein, peak 1 ($P_1$), contained no cholesterol. However, the protein in peaks 2 and 3 both contained cholesterol. From the higher ratio of protein to cholesterol in peak 2 (as compared with P3) it appeared likely that peak 2 represented HDL. The solutions contained the protein of peaks 1, 2 and 3 were concentrated by vacuum dialysis against 0.02M Tris/HCl, pH7.7 and subjected to acrylamide gel electrophoresis after prestaining with Sudan black B. After electrophoresis was completed the gels were overstained with amido black to reveal non-lipoprotein bands (FIG. 2).

Peak 2 material contained a single band which stained with both the lipid and protein stain, the mobility of this band was consistent with that of HDL. Peak 3 contained two protein bands both of which also reacted with the lipid stain, the mobility of these bands corresponded to that of LDL and VLDL. Peak 1 contained the normal serum proteins except for the lipoprotein components.

Figure 3:
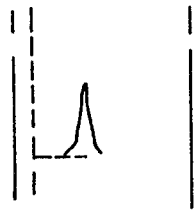
FIG. 3 is the schlieren pattern from the analytical ultracentrifuge run on a protein peak containing HDL ($P_2$).

When the peak 2 material was dialysed against 0.02M Tris/HCl, pH 7.7 containing 1% NaCl and subjected to ultracentrifugation a single symmetrical boundary was observed. (FIG. 3). The $S_{20w}$ value of this boundary (4.6S) matched that of HDL (4.9S).

EXAMPLE 6

Figure 4:
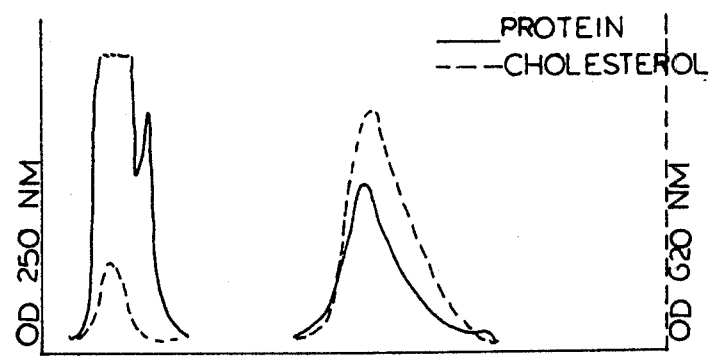
FIG. 4 is a plot of the cholesterol content of the protein fractions eluted from the sulphated ion exchanger of Example 6, below. This exchanger is less highly sulphated than that used in FIG. 1.

Chromatography was carried out as described above, but on a less highly sulphated ion exchanger (0.5 meq/g) only one lipoprotein peak bound on the column (FIG. 4).

Gel electrophoresis of the non-bound protein peak indicated that, in addition to the non-lipoproteins, it contained HDL. Electrophoresis further showed that the single bound peak consists of LDL and VLDL only.

EXAMPLE 7

Using a method based on that just described, 10 ml of serum was separated into two fractions on a 15 × 1 cm column (0.5 meq/g). The non-bound protein (serum proteins other than VLDL and LDL) was washed through in $MgCl_2$ while the bound fraction (LDL and VLDL) was eluted with 1M NaCl.

In order to determine the effect of the degree of sulphation on the binding of HDL, and LDL plus VLDL, a series of eight ion exchangers was prepared with between 0.1 and 3.75 meq/g. These eight, and a sample of SP-SEPHADEX (2.75 meq/g) were packed in columns made from Pasteur pipettes, equilibrated with 0.5M $MgCl_2$ and adjusted to the same levels (column volume 1.6 L ml).

The LDL and VLDL sample that was prepared above was dialysed against normal saline and then brought to 0.5M with respect to $MgCl_2$. An excess (approximately twice the saturating amount of this solution) was applied to each of the nine columns. The columns were washed with 20 ml of 0.5M $MgCl_2$ in order to remove all unbound LDL and VLDL. The bound LDL and VLDL were then eluted in 6 ml of 1M NaCl. The optical density at 280 m of this solution was used as a measure of the ion exchanger's capacity for LDL and VLDL.

Figure 5A:
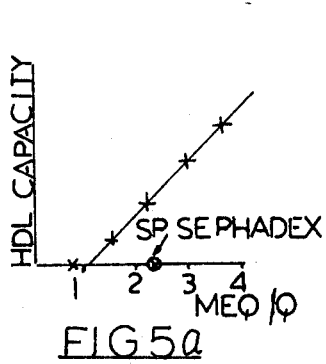
FIGS. 5a and 5b plot the ion exchanger's capacity for HDL, and VLDL plus LDL, respectively, as a function of the degree of sulphation of the ion exchanger and should be referred to in conjunction with Example 7.
Figure 5B:
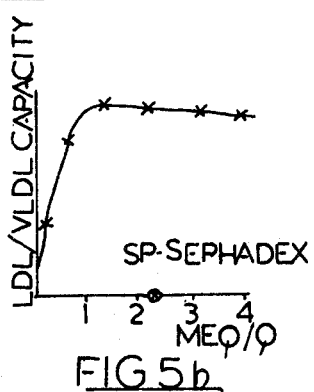

After reequiliberation of the ion exchangers the HDL plus serum non-lipoprotein fraction was applied to the columns in a similar manner, i.e., the ion exchangers were saturated with HDL and the bound HDL eluted in 6 ml of 1M NaCl. FIG. 5a shows the ion exchanger capacity for HDL and FIG. 5b for LDL plus VLDL as a function of the degree of sulphation. It can be seen that below 1 meq/g no HDL is bound. However, above this value HDL binding increases linearly with increasing the degree of sulphation. LDL and VLDL binding on the other hand, increases very rapidly between 0 and 1 meq/g and become nearly independent of the degree of sulphation above 1 meq/g. These results explain why the resin (3.7 meq/g) used in the first experiment described, bound with HDL, LDL and VLDL, while the ion exchanger (0.5 meq/g) used in the second case bound LDL and VLDL. It was further noted that the SP-SEPHADEX, FIG. 5b, bound no protein whatever under these conditions.

The results of capacity measurements of selected sulphated ion exchangers made in accordance with this procedure are set out in Table I.

TABLE I

| Sulphated Ion Exchangers Matrix | meq/g | Lipo-protein Capacity mg cholesterol/g |
|---|---|---|
| Microgranular Cellulose 10-50 | 2.24 | 25 |
| Microgranular Cellulose 10-00 | 2.11 | 18 |
| Microgranular Cellulose 50-00 | 2.06 | 2 |
| Regenerated cellulose 8-50 | 2.11 | 7.5 |
| Regenerated cellulose 10-00 | low | not tested |
| Regenerated cellulose 50-00 | 2.32 | 0.6 |
| Regenerated cellulose 100-00 | 1.53 | 0.2 |
| Cross-linked dextran LH-20 | 2.65 | 2.2 |
| G-25 | 2.38 | 0.7 |
| Cross-linked agarose | 3.1 | 5.2 |

The procedure was repeated using the serum from which the low density lipoproteins had been removed on the ultracentrifuge. This gave a measure of the ion exchangers capacity for HDL as none of the other serum proteins bound under these conditions.

What we claim is:

1. A method of selectively removing lipoproteins from blood plasma or serum which comprises the steps:
    a. adjusting the divalent cation concentration of a sample of blood plasma or serum to between 0.05 and 1.0M;

b. associating said sample with a cationic ion exchanger comprising a water insoluble, hydrophilic, water swellable matrix; a plurality of sulphate groups being chemically bonded to said matrix, the ion exchange capacity of said exchanger being provided by said sulphate groops; said matrix being a member selected from the group consisting of a cross-linked carbohydrate and a cross-linked carbohydrate substituted with hydroxy $C_2$–$C_4$ alkyl groups; and, c. recovering lipoproteins bound to said exchanger or recovering the blood serum or plasma residue from which only lipoproteins have been extracted or recovering both said extracted lipoproteins and said serum or plasma residue.

2. The method according to claim 1 wherein said cross-linked carbohydrate is a member of the group consisting of cross-linked polysaccharide and a derivative thereof, and said substituted cross-linked carbohydrate is a cross-linked polysaccharide derivative selected from the group consisting of an hydroxy $C_2$–$C_4$ alkyl derivative and any other derivative further substituted by hydroxy $C_2$–$C_4$ alkyl.

3. The method according to claim 1 wherein said cross-linked carbohydrate is a cross-linked cellulose in a form selected from the group consisting of native fibrous, microgranular, microcrystalline and regenerated forms and said substituted cross-linked carbohydrate is a cross-linked cellulose in a form selected from the group consisting of native fibrous, microgranular, microcrystalline and regenerated forms substituted by hydroxy $C_2$–$C_4$ alkyl.

4. The method according to claim 3 wherein said step of associating bood plasma or serum with a cationic ion exchanger comprises passing said plasma or serum through a column packed with said cationic exchanger.

5. The method according to claim 3 wherein residual blood plasma or serum from which lipoproteins have been removed is recovered and further treated to recover other components.

6. The method according to claim 3 wherein said hydroxy $C_2$–$C_4$ alkyl group is an hydroxy propyl group.

7. The method according to claim 2 wherein said step of associating blood plasma or serum with a cationic ion exchanger comprises passing said plasma or serum through at least one column packed with said cationic exchanger.

8. The method according to claim 2 wherein residual blood plasma or serum from which lipoproteins have been removed is recovered and further treated to recover other components.

9. The method according to claim 7 wherein said step of associating said plasma or serum with cationic ion exchanger comprises passing said plasma or serum through at least a pair of columns packed with said ion exchanger, said columns communicating in said series, the degree of sulphation of the ion exchanger in one column being less than in the other column.

10. The method according to claim 9 wherein the degree of sulphation in a first said column is selected to adsorb both the low density lipoprotein fraction and the very low density lipoprotein and the degree of sulphation in a second said column is selected to adsorb the high density lipoprotein fraction.

11. The method according to claim 2 wherein the matrix is agar, agarose or dextran.

12. The method according to claim 11 wherein said matrix is cross-linked by a bi-functional compound of the formula X-R-Y wherein X and Y are halo or epoxy groups and R is a residual aliphatic group of from 3 to 10 carbon atoms which may also be substituted with ether or hydroxy groups.

13. The method according to claim 12 wherein said bifunctional compound is epichlorohydrin.

14. The method according to claim 2 wherein said hydroxy $C_2$–$C_4$ alkyl group is an hydroxy propyl group.

15. The method according to claim 3 wherein said matrix is cross-linked microgranular or microcrystalline cellulose, the degree of cross-linking being less than 15%.

16. The method according to claim 3 wherein said matrix is regenerated cellulose cross-linked with epichlorohydrin and having pendant hydroxypropyl groups bonded thereto.

17. The method according to claim 16 wherein said matrix is sulphated with up to 5.5 meq/g (sulphate/ion exchanger).

* * * * *